(12) United States Patent
Yamanaka et al.

(10) Patent No.: US 9,795,710 B2
(45) Date of Patent: Oct. 24, 2017

(54) METHOD OF FABRICATING SCAFFOLD FOR TISSUE ENGINEERING

(71) Applicant: GC Corporation, Tokyo (JP)

(72) Inventors: Katsuyuki Yamanaka, Tokyo (JP); Yuuhiro Sakai, Tokyo (JP); Yusuke Shigemitsu, Tokyo (JP)

(73) Assignee: GC Corporation, Tokyo (JP)

( * ) Notice: Subject to any disclaimer, the term of this patent is extended or adjusted under 35 U.S.C. 154(b) by 0 days.

(21) Appl. No.: 15/168,360

(22) Filed: May 31, 2016

(65) Prior Publication Data

US 2016/0367721 A1    Dec. 22, 2016

(30) Foreign Application Priority Data

Jun. 18, 2015  (JP) ................ 2015-123277

(51) Int. Cl.
*A61L 27/18* (2006.01)
*A61L 27/34* (2006.01)
*A61L 27/54* (2006.01)
*A61L 27/56* (2006.01)

(52) U.S. Cl.
CPC ............... *A61L 27/18* (2013.01); *A61L 27/34* (2013.01); *A61L 27/54* (2013.01); *A61L 27/56* (2013.01); *A61L 2430/00* (2013.01)

(58) Field of Classification Search
None
See application file for complete search history.

(56) References Cited

U.S. PATENT DOCUMENTS

| 2005/0271701 | A1 | 12/2005 | Cottone, Jr. et al. |
| 2006/0083771 | A1 | 4/2006 | Yamamoto et al. |
| 2012/0290075 | A1 | 11/2012 | Mortisen et al. |

FOREIGN PATENT DOCUMENTS

JP    2006-136673    6/2006

OTHER PUBLICATIONS

Subbu S Venkatraman et al: "Biodegradable stents with elastic memory" Biomaterials, Elsevier Science Publishers BV., Barking, GB, vol. 27, No. 8, Mar. 1, 2006, pp. 1573-1578.
F. Yang et al: "Fabrication of nano-structured porous PLLA scaffold intended for nerve tissue engineering" Biomaterials, Elsevier Science Publishers BV., Barking, GB, vol. 25, No. 10, May 1, 2004, pp. 1891-1900.
E.B. Lavik et al: "Fabrication of degradable polymer scaffolds to direct the integration and differentiation of retinal progenitors" Biomaterials, Elsevier Science Publishers BV., Barking, GB, vol. 26, No. 16, Jun. 1, 2005, pp. 3187-3196.
Eun Jin Kim et al: "Preparation of biodegradable PLA/PLGA membranes with PGA mesh and their application for periodontal guided tissue regeneration" Biomedical Materials, Institute of Physics Publishing, Bristol, GB, vol. 4, No. 5, Oct. 1, 2009, pp. 055001 (7pp).

*Primary Examiner* — Mina Haghighatian
*Assistant Examiner* — Luke Karpinski
(74) *Attorney, Agent, or Firm* — IPUSA, PLLC

(57) ABSTRACT

A method of fabricating a scaffold for tissue engineering that includes a frame structure including one of poly-D-lactic acid and poly-L-lactic acid and a coating layer formed on a surface of the frame structure and including a lactic acid-glycolic acid copolymer. The method includes mixing a first granular porous substance including one of poly-D-lactic acid and poly-L-lactic acid with a second granular porous substance including the lactic acid-glycolic acid copolymer to prepare a mixture, and pressurizing and heating the mixture in a mold. In the heating, the mixture is heated to a temperature greater than or equal to the melting point of the lactic acid-glycolic acid copolymer and less than the melting point of one of poly-D-lactic acid and poly-L-lactic acid.

1 Claim, 1 Drawing Sheet

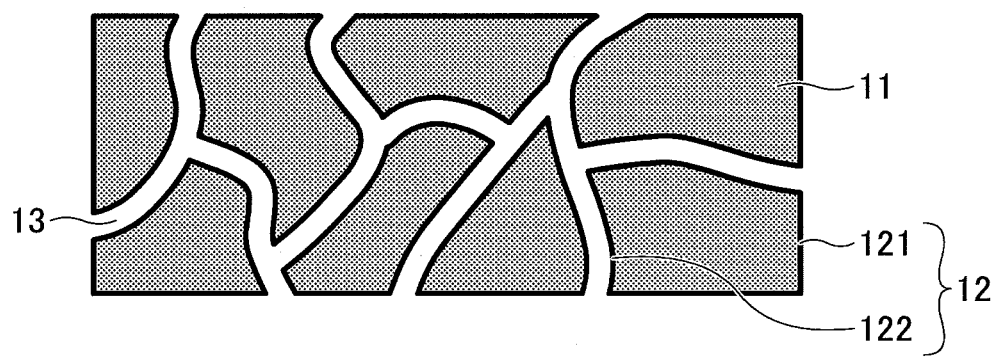

METHOD OF FABRICATING SCAFFOLD FOR TISSUE ENGINEERING

CROSS-REFERENCE TO RELATED APPLICATION

The present application is based upon and claims the benefit of priority of Japanese Patent Application No. 2015-123277, filed on Jun. 18, 2015, the entire contents of which are incorporated herein by reference.

BACKGROUND OF THE INVENTION

1. Field of the Invention

An aspect of this disclosure relates to a method of fabricating a scaffold for tissue engineering.

2. Description of the Related Art

There exists a treatment where body tissue lost due to, for example, surgery or an injury is regenerated using somatic cells or stem cells, and the body tissue is transplanted into a patient to recover the lost body tissue. To regenerate body tissue in this treatment, a scaffold (matrix) is necessary to support inoculated cells until the body tissue is regenerated by the cells.

For example, Japanese Laid-Open Patent Publication No. 2006-136673 discloses a block-shaped scaffold for tissue engineering made of a bioabsorbable polymer. The disclosed block-shaped scaffold for tissue engineering has a three-dimensional porous open-pore structure with a pore diameter of 5 to 50 μm and irregular interconnected pores that occupy 20 to 80% of the cross-sectional area of the block-shaped scaffold for tissue engineering. Also, the block-shaped scaffold for tissue engineering has an elastic modulus of 0.1 to 2.5 MPa, and a modulus of volume change of 95 to 105% when immersed in water for 24 hours. Japanese Laid-Open Patent Publication No. 2006-136673 also discloses polyglycolic acid and polylactic acid as examples of bioabsorbable polymers.

Compared with a sponge-like scaffold for tissue engineering, the disclosed block-shaped scaffold for tissue engineering has a higher elastic modulus that provides excellent shape stability, and does not greatly change in shape even when it absorbs water.

Here, there is a demand for a scaffold for tissue engineering that can maintain its structure even when used to culture and differentiate cells over a long period of time, and has an excellent cell differentiation potency.

SUMMARY OF THE INVENTION

In an aspect of this disclosure, there is provided a method of fabricating a scaffold for tissue engineering that includes a frame structure including one of poly-D-lactic acid and poly-L-lactic acid and a coating layer formed on a surface of the frame structure and including a lactic acid-glycolic acid copolymer. The method includes mixing a first granular porous substance including one of poly-D-lactic acid and poly-L-lactic acid with a second granular porous substance including the lactic acid-glycolic acid copolymer to prepare a mixture, and pressurizing and heating the mixture in a mold. In the heating, the mixture is heated to a temperature greater than or equal to the melting point of the lactic acid-glycolic acid copolymer and less than the melting point of one of poly-D-lactic acid and poly-L-lactic acid.

BRIEF DESCRIPTION OF THE DRAWINGS

FIG. 1 is a schematic cross-sectional view of a scaffold for tissue engineering according to an embodiment.

DESCRIPTION OF THE PREFERRED EMBODIMENTS

According to research conducted by the inventors of the present invention, a block-shaped scaffold for tissue engineering fabricated according to Japanese Laid-Open Patent Publication No. 2006-136673 by using polylactic acid as a bioabsorbable polymer material can maintain its structure even when used to culture cells over a long time.

However, according to the research, a block-shaped scaffold for tissue engineering fabricated by using polylactic acid as a bioabsorbable polymer does not always have a sufficient cell differentiation potency.

Embodiments of the present invention are described below. However, the present invention is not limited to those embodiments, and variations and modifications may be made without departing from the scope of the present invention.

First Embodiment

An exemplary method of fabricating a scaffold for tissue engineering according to a first embodiment is described below.

A scaffold for tissue engineering fabricated by the method of the first embodiment may include a frame structure including poly-D-lactic acid or poly-L-lactic acid, and a coating layer formed on a surface of the frame structure and including lactic acid-glycolic acid copolymer. The method may include the following processes:

A mixing process of mixing a first granular porous substance including poly-D-lactic acid or poly-L-lactic acid with a second granular porous substance including lactic acid-glycolic acid copolymer to prepare a mixture.

A pressurizing-heating process of pressurizing and heating the mixture placed in a mold.

In the pressurizing-heating process, the mixture may be heated to a temperature that is greater than or equal to the melting point of lactic acid-glycolic acid copolymer and less than the melting point of poly-D-lactic acid or poly-L-lactic acid included in the first granular porous substance.

First, a scaffold for tissue engineering that can be fabricated by the method of the present embodiment is described.

A scaffold for tissue engineering producible by the method of the present embodiment may include a frame structure including poly-D-lactic acid or poly-L-lactic acid, and a coating layer formed on a surface of the frame structure and including lactic acid-glycolic acid copolymer.

Thus, the scaffold for tissue engineering of the present embodiment may include a frame structure including poly-D-lactic acid or poly-L-lactic acid.

The frame structure has a three-dimensional porous open-pore structure including irregular interconnected pores. According to research conducted by the inventors of the present invention, including poly-D-lactic acid or poly-L-lactic acid in a frame structure makes it possible to improve the strength of the frame structure and to achieve long-term structural stability of the frame structure during cell culture.

As a type of polylactic acid, poly-DL-lactic acid, which includes both D-lactic acid and L-lactic acid at the same time in the molecular chain, is also known. However, compared with a frame structure including poly-D-lactic acid or poly-L-lactic acid, a frame structure including poly-DL-lactic acid does not have sufficient long-term structural stability during cell culture. For this reason, the frame structure of the present embodiment preferably includes poly-D-lactic acid or poly-L-lactic acid.

More preferably, the frame structure of the present embodiment is made of poly-D-lactic acid or poly-L-lactic acid. However, the frame structure may include an inevitable component that inevitably enters the frame structure during, for example, a production process.

Next, the coating layer is described. The coating layer may include lactic acid-glycolic acid copolymer. According to research conducted by the inventors of the present invention, when used for the frame structure, lactic acid-glycolic acid copolymer provides less long-term structural stability during cell culture compared with poly-D-lactic acid and poly-L-lactic acid. However, because lactic acid-glycolic acid copolymer has excellent capability in holding cells to be cultured, including lactic acid-glycolic acid copolymer in the coating layer coating the surface of the frame structure makes it possible to improve the differentiation potency of the scaffold for tissue engineering.

The coating layer is preferably made of lactic acid-glycolic acid copolymer. Even in this case, however, the coating layer may include an inevitable component that inevitably enters the coating layer during, for example, a production process.

Next, an exemplary structure of the scaffold for tissue engineering of the present embodiment is described. FIG. 1 is a schematic cross-sectional view of the scaffold for tissue engineering of the present embodiment.

As described above, the scaffold for tissue engineering has a three-dimensional porous open-pore structure including irregular interconnected pores. In FIG. 1, for illustration purposes, the size of the irregular interconnected pores is made larger than their actual size with respect to the size of the cross section. The actual size of the interconnected pores is very small.

As illustrated by FIG. 1, a scaffold for tissue engineering 10 of the present embodiment includes a frame structure 11 and a coating layer 12 formed on a surface(s) of the frame structure 11. The frame structure 11 includes irregular interconnected pores 13.

As illustrated by FIG. 1, the coating layer 12 may include an outer coating layer 121 formed on an outer surface(s) of the frame structure 11, as well as an inner coating layer 122 formed on an inner surface(s) of the interconnected pores 13 in the frame structure 11.

In the example of FIG. 1, the outer coating layer 121 is formed on the entire outer surface of the frame structure 11, and the inner coating layer 122 is formed on the entire inner surface of the interconnected pores 13 in the frame structure 11. However, the present invention is not limited to this example.

For example, the outer coating layer 121 and/or the inner coating layer 122 may be formed such that a part of the surface of the frame structure 11 is left uncovered or exposed.

As described above, including poly-D-lactic acid or poly-L-lactic acid in a frame structure can improve the strength of the frame structure and give long-term structural stability during cell culture to the frame structure. However, the cell differentiation potency of such a frame structure is still insufficient. For this reason, in the present embodiment, the coating layer 12 including lactic acid-glycolic acid copolymer is provided on the frame structure 11 to improve the cell differentiation potency. Even when the coating layer 12 does not completely cover the surface of the frame structure 11, compared with a configuration where a scaffold for tissue engineering is composed only of a frame structure including poly-D-lactic acid or poly-L-lactic acid, the configuration of the present embodiment makes it possible to improve the cell differentiation potency of the scaffold for tissue engineering 10 in addition to its long-term structural stability during cell culture.

The proportion of the coating layer 12 in the scaffold for tissue engineering 10 is not limited to any specific value, and can be determined based on, for example, the type or purpose of cells to be cultured. However, to improve the differentiation potency during cell culture, the amount of the coating layer 12 in the scaffold 10 is preferably greater than or equal to 1 mass %, and more preferably greater than or equal to 3 mass %.

The maximum amount of the coating layer 12 in the scaffold for tissue engineering 10 is not limited to any specific value. However, the amount of the coating layer 12 in the scaffold for tissue engineering 10 is preferably less than or equal to 50 mass %, and more preferably less than or equal to 30 mass %.

Next, the method of fabricating the scaffold for tissue engineering of the present embodiment is described in detail.

The method of fabricating the scaffold for tissue engineering of the present embodiment may include the following processes:

A mixing process of mixing a first granular porous substance including poly-D-lactic acid or poly-L-lactic acid with a second granular porous substance including lactic acid-glycolic acid copolymer to prepare a mixture.

A pressurizing-heating process of pressurizing and heating the mixture placed in a mold.

Each of the processes is described below.

Mixing Process

In the mixing process, a first granular porous substance including poly-D-lactic acid or poly-L-lactic acid is mixed with a second granular porous substance including lactic acid-glycolic acid copolymer to prepare a mixture.

The first granular porous substance may be any type of granular substance that includes poly-D-lactic acid or poly-L-lactic acid and has a porous structure.

For example, the first granular porous substance may be prepared as described below.

First, poly-D-lactic acid or poly-L-lactic acid is dissolved in an organic solvent (dissolution step). Any organic solvent that can dissolve poly-D-lactic acid or poly-L-lactic acid may be used. For example, the organic solvent preferably includes at least one of chloroform, dichloromethane, carbon tetrachloride, acetone, dioxane, and tetrahydrofuran.

When dissolving poly-D-lactic acid or poly-L-lactic acid in the organic solvent, heat treatment or ultrasonic treatment may also be performed. The concentration of poly-D-lactic acid or poly-L-lactic acid in a solution obtained by dissolving poly-D-lactic acid or poly-L-lactic acid is not limited to any specific value, and may be determined so that poly-D-lactic acid or poly-L-lactic acid can be uniformly dispersed in the organic solvent. Preferably, the amount of poly-D-lactic acid or poly-L-lactic acid in the organic solvent is greater than or equal to 1 mass % and less than or equal to 20 mass %.

Next, particulates are added to and mixed with the solution containing poly-D-lactic acid or poly-L-lactic acid (particulate addition step). The particulates do not dissolve in the organic solvent in the solution, but dissolve in a liquid that does not dissolve poly-D-lactic acid or poly-L-lactic acid.

The particulates are preferably, but are not limited to, a water-soluble organic/inorganic salt such as sodium chloride, potassium chloride, calcium chloride, ammonium chloride, or trisodium citrate.

The diameter of the particulates is preferably greater than or equal to 100 μm and less than or equal to 2000 μm, and more preferably greater than or equal to 200 μm and less than or equal to 1000 μm.

The amount of added particulates with respect to the solution containing poly-D-lactic acid or poly-L-lactic acid is not limited to any specific value, and may be determined according to the required density of a scaffold for tissue engineering to be fabricated. The concentration of the particulates in the solution containing poly-D-lactic acid or poly-L-lactic acid is preferably greater than or equal to 1.0 $g/cm^3$ and less than or equal to 1.5 $g/cm^3$, and more preferably greater than or equal to 1.0 $g/cm^3$ and less than or equal to 1.25 $g/cm^3$.

With the concentration of the particulates set at a value greater than or equal to 1.0 $g/cm^3$, a poly-D-lactic acid/poly-L-lactic acid structure including the particulates becomes very hard, and this in turn makes it easier to grind the poly-D-lactic acid/poly-L-lactic acid structure in a grinding step described later. With the concentration of the particulates set at a value less than or equal to 1.5 $g/cm^3$, the proportion of poly-D-lactic acid or poly-L-lactic acid in a poly-D-lactic acid/poly-L-lactic acid structure including the particulates obtained after a freeze-drying step (described later) becomes sufficiently high, and this in turn makes it possible to increase the yield.

For example, the particulates may be substantially uniformly mixed with the solution containing poly-D-lactic acid or poly-L-lactic acid by adding the particulates to the solution, agitating the solution as necessary, and then pouring the solution into a mold. Also, the particulates may be mixed with the solution containing poly-D-lactic acid or poly-L-lactic acid by pouring the solution into a mold containing the particulates. Further, the particulates may be mixed with the solution containing poly-D-lactic acid or poly-L-lactic acid by putting the particulates into a mold containing the solution.

Next, the solution containing the particulates and poly-D-lactic acid or poly-L-lactic acid is frozen and then dried to remove the organic solvent (freeze-drying step).

As a result of the freeze-drying step, a porous poly-D-lactic acid/poly-L-lactic acid structure including the particulates is obtained. At this stage, the particulates are included in the poly-D-lactic acid/poly-L-lactic acid structure in the form of solid.

Next, the poly-D-lactic acid/poly-L-lactic acid structure including the particulates is ground into granules (grinding step). Because the particulates exist in the poly-D-lactic acid/poly-L-lactic acid structure in the form of solid (particles), the poly-D-lactic acid/poly-L-lactic acid structure becomes hard and can be easily ground into granules with a desired diameter.

Next, from the granules obtained by grinding the poly-D-lactic acid/poly-L-lactic acid structure including the particulates, the particulates are removed by using a solution that does not dissolve poly-D-lactic acid or poly-L-lactic acid (particulate removing step).

The method of removing the particulates may vary depending on the substance forming the particulates. However, when the particulates are formed of a water-soluble organic/inorganic salt such as sodium chloride, potassium chloride, calcium chloride, ammonium chloride, or trisodium citrate, the particulates can be dissolved and removed with water.

Through the above steps, a first granular porous substance (granules) is prepared. The first granular porous substance preferably includes poly-D-lactic acid or poly-L-lactic acid, and more preferably made of poly-D-lactic acid or poly-L-lactic acid. Still, however, the first granular porous substance may include an inevitable component such as a residue of the particulates that remains after the above steps.

After removing the particulates, the granules may be screened (or sieved) to obtain the first granular porous substance with a desired diameter.

The diameter of the first granular porous substance supplied to a pressurizing-heating step described later is preferably greater than or equal to 100 μm and less than or equal to 3000 μm.

The scaffold for tissue engineering of the present embodiment includes interconnected pores so that cells can be held in the interconnected pores. This configuration makes it possible to improve the efficiency of cell culture. According to research conducted by the inventors of the present invention, a number of interconnected pores sufficient to improve the efficiency of cell culture can be formed in the scaffold for tissue engineering by making the diameter of the first granular porous substance supplied to the pressurizing-heating step greater than or equal to 100 μm and less than or equal to 3000 μm.

The second granular porous substance may be any type of granular substance that includes lactic acid-glycolic acid copolymer and has a porous structure, and may be prepared by any appropriate method. For example, the second granular porous substance may be prepared by a method similar to the method of preparing the first granular porous substance described above, by dissolving lactic acid-glycolic acid copolymer instead of poly-D-lactic acid or poly-L-lactic acid at the dissolution step.

The second granular porous substance preferably includes lactic acid-glycolic acid copolymer, and is more preferably made of lactic acid-glycolic acid copolymer. Still, however, the second granular porous substance may include an inevitable component such as a residue of particulates that remains after the preparation steps.

Then, a mixture is prepared by mixing the first granular porous substance and the second granular porous substance prepared as described above.

The proportions of the first granular porous substance and the second granular porous substance in the mixture may be determined at any appropriate values. For example, the proportion of the second granular porous substance in the mixture is preferably greater than or equal to 1 mass % and less than or equal to 50 mass %, and more preferably greater than or equal to 3 mass % and less than or equal to 30 mass %.

Setting the proportion of the second granular porous substance at a value greater than or equal to 1 mass % makes it possible to form a uniform coating layer and thereby makes it possible to improve the cell differentiation potency. Also, setting the proportion of the second granular porous substance at a value less than or equal to 50 mass % makes it possible to improve the strength and the long-term structural stability of the frame structure.

The first granular porous substance and the second granular porous substance may be mixed by any appropriate method for mixing solids.

Pressurizing-Heating Process

Next, a pressurizing-heating process is described. In the pressurizing-heating process, the mixture is placed in a mold, and pressurized and heated.

Although the pressurization condition in the pressurizing-heating process may vary depending on the shape and size of a frame structure to be produced, the pressurization condition is preferably greater than or equal to 500 g/cm$^2$ and less than or equal to 3000 g/cm$^2$, and more preferably greater than or equal to 1000 g/cm$^2$ and less than or equal to 2000 g/cm$^2$.

Setting the pressurization condition at a value greater than or equal to 500 g/cm$^2$ makes it possible to improve the shape stability of the frame structure, and setting the pressurization condition at a value less than or equal to 3000 g/cm$^2$ makes it possible to form a sufficient number of interconnected pores for growing cells.

The heating temperature in the pressurizing-heating process is preferably greater than or equal to the melting point of lactic acid-glycolic acid copolymer and less than the melting point of poly-D-lactic acid or poly-L-lactic acid included in the first granular porous substance. More specifically, the heating temperature is preferably greater than or equal to 40° C. and less than or equal to 105° C., and more preferably greater than or equal to 55° C. and less than or equal to 95° C. By heating the mixture at a temperature greater than or equal to the melting point of lactic acid-glycolic acid copolymer and less than the melting point of poly-D-lactic acid or poly-L-lactic acid included in the first granular porous substance, it is possible to melt only lactic acid-glycolic acid copolymer in the mixture while maintaining the frame structure. Consequently, lactic acid-glycolic acid copolymer wets and spreads over the surface of the frame structure and forms a coating layer. As a result, a scaffold for tissue engineering, which includes the frame structure including poly-D-lactic acid or poly-L-lactic acid and the coating layer formed on the surface of the frame structure and including lactic acid-glycolic acid copolymer, is produced.

As described above, the scaffold for tissue engineering fabricated by the method of the present embodiment includes a frame structure having long-term structural stability during cell culture, and a coating layer that is formed on a surface of the frame structure and can facilitate the differentiation of cells. Thus, the method of the present embodiment can fabricate a scaffold for tissue engineering that has both long-term structural stability during cell culture and excellent cell differentiation potency.

Second Embodiment

An exemplary method of fabricating a scaffold for tissue engineering according to a second embodiment is described below.

A scaffold for tissue engineering fabricated by the method of the second embodiment may include a frame structure including poly-D-lactic acid or poly-L-lactic acid, and a coating layer formed on a surface of the frame structure and including lactic acid-glycolic acid copolymer. The method may include the following processes:

A frame structure preparation process of preparing a frame structure including poly-D-lactic acid or poly-L-lactic acid.

A heating process of heating the frame structure after dispersing powder of lactic acid-glycolic acid copolymer on a surface of the frame structure.

In the heating process, the frame structure may be heated to a temperature that is greater than or equal to the melting point of lactic acid-glycolic acid copolymer and less than the melting point of poly-D-lactic acid or poly-L-lactic acid included in the frame structure.

Each of the processes is described below.

<Frame Structure Preparation Process>

First, the frame structure preparation process is described. In the frame structure preparation process, a frame structure including poly-D-lactic acid or poly-L-lactic acid is prepared.

The frame structure preferably has a three-dimensional porous open-pore structure including irregular interconnected pores.

For example, the frame structure may be prepared as described below.

The frame structure may be prepared by placing porous granules including poly-D-lactic acid or poly-L-lactic acid (poly-D-lactic acid/poly-L-lactic acid granules) in a desired mold, and pressurizing and heating the granules (pressurizing-heating step).

The poly-D-lactic acid/poly-L-lactic acid granules may be prepared by substantially the same method as the method of preparing the first granular porous substance described in the first embodiment, and therefore descriptions of the method are omitted here.

Although the pressurization condition in the pressurizing-heating step may vary depending on the shape and size of a frame structure to be prepared, the pressurization condition is preferably greater than or equal to 500 g/cm$^2$ and less than or equal to 3000 g/cm$^2$, and more preferably greater than or equal to 1000 g/cm$^2$ and less than or equal to 2000 g/cm$^2$. Setting the pressurization condition at a value greater than or equal to 500 g/cm$^2$ makes it possible to improve the shape stability of the frame structure, and setting the pressurization condition at a value less than or equal to 3000 g/cm$^2$ makes it possible to form a sufficient number of interconnected pores for growing cells.

The heating condition in this step may also vary depending on the shape and size of the frame structure. When the poly-D-lactic acid/poly-L-lactic acid granules are to be heated under the above pressurization condition while maintaining their volume, the heating condition is preferably greater than or equal to 60° C. and less than or equal to 200° C.

Heating the poly-D-lactic acid/poly-L-lactic acid granules at a temperature greater than or equal to 60° C. makes it possible to increase the bond between the poly-D-lactic acid/poly-L-lactic acid granules, and thereby makes it possible to improve the shape stability of the frame structure. Also, heating the poly-D-lactic acid/poly-L-lactic acid granules at a temperature less than or equal to 200° C. makes it possible to prevent denaturation of poly-D-lactic acid or poly-L-lactic acid.

<Heating Process>

Next, the heating process is described. In the heating process, the frame structure is heated after dispersing powder of lactic acid-glycolic acid copolymer on a surface of the frame structure.

The particle diameter of powder of lactic acid-glycolic acid copolymer dispersed on the surface of the frame structure is not limited to any specific value. However, powder of lactic acid-glycolic acid copolymer with a small particle diameter is preferable because it can easily enter interconnected pores in the frame structure and can form a uniform coating layer on the surface of the frame structure.

For example, the average particle diameter of the powder of lactic acid-glycolic acid copolymer is preferably greater than or equal to 100 μm and less than or equal to 710 μm, and more preferably greater than or equal to 150 μm and less than or equal to 500 μm.

Here, the average particle diameter is represented by a particle diameter at a cumulative volume of 50% in a particle size distribution obtained by a laser diffraction and scattering method.

The amount of the powder of lactic acid-glycolic acid copolymer dispersed on the frame structure may be determined at any appropriate value. For example, the proportion of the powder of lactic acid-glycolic acid copolymer in the total mass of the frame structure and the powder of lactic acid-glycolic acid copolymer is preferably greater than or equal to 1 mass % and less than or equal to 50 mass %, and more preferably greater than or equal to 3 mass % and less than or equal to 30 mass %.

Setting the proportion of the powder of lactic acid-glycolic acid copolymer at a value greater than or equal to 1 mass % makes it possible to form a uniform coating layer and thereby makes it possible to improve the cell differentiation potency. Also, setting the proportion of the powder of lactic acid-glycolic acid copolymer at a value less than or equal to 30 mass % makes it possible to improve the strength and the long-term structural stability of the frame structure.

After the powder of lactic acid-glycolic acid copolymer is dispersed on the surface of the frame structure, the frame structure is heated. The heating temperature in the heating process is preferably greater than or equal to the melting point of lactic acid-glycolic acid copolymer and less than the melting point of poly-D-lactic acid or poly-L-lactic acid included in the frame structure. More specifically, the heating temperature is preferably greater than or equal to 40° C. and less than or equal to 105° C., and more preferably greater than or equal to 55° C. and less than or equal to 95° C.

By heating the frame structure at a temperature greater than or equal to the melting point of lactic acid-glycolic acid copolymer and less than the melting point of poly-D-lactic acid or poly-L-lactic acid included in the frame structure, it is possible to melt only lactic acid-glycolic acid copolymer dispersed on the surface of the frame structure while maintaining the frame structure itself. Consequently, lactic acid-glycolic acid copolymer wets and spreads over the surface of the frame structure and forms a coating layer. As a result, a scaffold for tissue engineering, which includes the frame structure including poly-D-lactic acid or poly-L-lactic acid and the coating layer formed on the surface of the frame structure and including lactic acid-glycolic acid copolymer, is produced.

The scaffold for tissue engineering fabricated by the method of the second embodiment has substantially the same configuration as that of the scaffold for tissue engineering fabricated by the method of the first embodiment. Accordingly, the scaffold for tissue engineering fabricated by the method of the second embodiment also includes a frame structure having long-term structural stability during cell culture, and a coating layer that is formed on a surface of the frame structure and can facilitate the differentiation of cells. Thus, the method of the second embodiment can also fabricate a scaffold for tissue engineering that has both long-term structural stability during cell culture and excellent cell differentiation potency.

EXAMPLES

Examples below are provided to facilitate understanding of the present invention. However, the present invention is not limited to those examples.

Example 1

A scaffold for tissue engineering was fabricated as described below.
(Mixing Process)

A first granular porous substance made of poly-L-lactic acid was prepared through the steps described below.

First, poly-L-lactic acid (about 250,000 weight-average molecular weight) was added to 1,4-dioxane such that the concentration of poly-L-lactic acid would become 6 mass %, and the resulting mixture was agitated with an agitator to dissolve poly-L-lactic acid and obtain a 1,4-dioxane solution containing poly-L-lactic acid (dissolution step).

Next, trisodium citrate powder (with a particle diameter between 200 μm and 500 μm) was substantially uniformly mixed with the 1,4-dioxane solution containing poly-L-lactic acid such that the concentration of trisodium citrate powder would become about 1.02 $g/cm^3$ (particulate addition step), and the resulting solution was poured into a mold.

The solution was frozen at −30° C. using a freezer (SANYO Electric Co., Ltd., product name: MDF-0281AT). Then, the frozen solution was dried for 48 hours under reduced pressure using a vacuum dryer (Yamato Scientific Co., Ltd., product name: DP43) to remove 1,4-dioxane and obtain a polymer material of poly-L-lactic acid substantially uniformly containing trisodium citrate powder (freeze-drying step). The polymer material was cut into pieces, and the pieces were ground for 20 minutes using a planetary pot mill (grinding step).

The ground polymer material was put into a flask, distilled water was added to the flask, and the resulting mixture was agitated to remove trisodium citrate powder (particulate removing step). After removing trisodium citrate powder, the ground polymer material was placed in a petri dish and was dried for 48 hours using a vacuum drier. Then, the ground and dried polymer material was screened to obtain a first granular porous substance (granules) made of poly-L-lactic acid and having a particle diameter between 700 μm and 1400 μm and an average pore diameter of about 5 μm.

A second granular porous substance was prepared by a method similar to the above-described method of preparing the first granular porous substance except that lactic acid-glycolic acid copolymer was added to 1,4-dioxane at a concentration of 6 mass % in the dissolution step.

A mixture was prepared by mixing the first granular porous substance and the second granular porous substance such that the proportion of the second granular porous substance in the mixture would become 10 mass %.
(Pressurizing-Heating Process)

The prepared mixture was placed in a glass container with an inside diameter of 9 mm and a height of 10 mm up to a height of about 7 mm. Then, the mixture was heated at 50° C. for 20 minutes, while maintaining the volume of the mixture being pressurized at 1500 $g/cm^2$ by a titanium rod having a diameter of 9 mm. As a result, a columnar scaffold for tissue engineering with a diameter of 9 mm and a height of about 7 mm was obtained.

Example 2

In Example 2, a scaffold for tissue engineering was fabricated and evaluated in substantially the same manner as in Example 1 except that a first granular porous substance made of poly-D-lactic acid was used.

The first granular porous substance made of poly-D-lactic acid was prepared by a method similar to the method of preparing the first granular porous substance made of poly-L-lactic acid in Example 1 except that in the dissolution step, poly-D-lactic acid (about 250,000 weight-average molecular weight) was added to 1,4-dioxane such that the concentration of poly-D-lactic acid would become 6 mass % and the resulting mixture was agitated with an agitator.

Example 3

A scaffold for tissue engineering was fabricated as described below.
(Frame Structure Preparation Process)

A frame structure preparation process was performed as described below to prepare a frame structure including poly-L-lactic acid.

First, poly-L-lactic acid (about 250,000 weight-average molecular weight) was added to 1,4-dioxane such that the concentration of poly-L-lactic acid would become 6 mass %, and the resulting mixture was agitated with an agitator to dissolve poly-L-lactic acid and obtain a 1,4-dioxane solution containing poly-L-lactic acid (dissolution step).

Next, trisodium citrate powder (with a particle diameter between 200 μm and 500 μm) was substantially uniformly mixed with the 1,4-dioxane solution containing poly-L-lactic acid such that the concentration of trisodium citrate powder would become about 1.02 g/cm$^3$ (particulate addition step), and the resulting solution was poured into a mold.

The solution was frozen at −30° C. using a freezer (SANYO Electric Co., Ltd., product name: MDF-0281AT). Then, the frozen solution was dried for 48 hours under reduced pressure using a vacuum dryer (Yamato Scientific Co., Ltd., product name: DP43) to remove 1,4-dioxane and obtain a polymer material of poly-L-lactic acid substantially uniformly containing trisodium citrate powder (freeze-drying step).

The polymer material was cut into pieces, and the pieces were ground for 20 minutes using a planetary pot mill (grinding step).

The ground polymer material was put into a flask, distilled water was added to the flask, and the resulting mixture was agitated to remove trisodium citrate powder (particulate removing step). After removing trisodium citrate powder, the ground polymer material was placed in a petri dish and was dried for 48 hours using a vacuum drier. Then, the ground and dried polymer material was screened to obtain porous poly-L-lactic acid granules with a diameter between 700 μm and 1400 μm and an average pore diameter of about 5 μm.

The obtained porous poly-L-lactic acid granules were placed in a glass container with an inside diameter of 9 mm and a height of 10 mm up to a height of about 7 mm. The porous poly-L-lactic acid granules were heated at 180° C. for 30 minutes, while maintaining the volume of the porous poly-L-lactic acid granules being pressurized at 1500 g/cm$^2$ by a glass rod having a diameter of 9 mm (pressurizing-heating step), to obtain a columnar frame structure with a diameter of 9 mm and a height of about 4 mm.

The obtained frame structure was observed with an electron microscope, and it was confirmed that the frame structure had a three-dimensional porous open-pore structure having pores in partitioning walls and also including irregular interconnected pores.
(Heating Process)

Next, the obtained frame structure was placed in a heating furnace for heat processing, and powder of lactic acid-glycolic acid copolymer with an average particle diameter of 200 μm was dispersed on the surface of the frame structure. The powder of lactic acid-glycolic acid copolymer was dispersed such that the proportion of the powder of lactic acid-glycolic acid copolymer in the total mass of the frame structure and the powder of lactic acid-glycolic acid copolymer would become 20 mass %.

Then, the frame structure with the powder of lactic acid-glycolic acid copolymer was heated at 95° C. for 20 minutes to obtain a scaffold for tissue engineering.

Example 4

In Example 4, a scaffold for tissue engineering was fabricated and evaluated in substantially the same manner as in Example 3 except that a frame structure including poly-D-lactic acid was used.

The frame structure including poly-D-lactic acid was prepared in substantially the same manner as in Example 3 except that in the dissolution step of the frame structure preparation process, poly-D-lactic acid (about 250,000 weight-average molecular weight) was added to 1,4-dioxane such that the concentration of poly-D-lactic acid would become 6 mass % and the resulting mixture was agitated with an agitator.

An aspect of this disclosure makes it possible to provide a method of fabricating a scaffold for tissue engineering that has both long-term structural stability during cell culture and excellent cell differentiation potency.

Methods of fabricating a scaffold for tissue engineering according to embodiments are described above. However, the present invention is not limited to the specifically disclosed embodiments, and variations and modifications may be made without departing from the scope of the present invention.

What is claimed is:

1. A method of fabricating a scaffold for tissue engineering that includes a frame structure including one of poly-D-lactic acid and poly-L-lactic acid and a coating layer formed on a surface of the frame structure and including a lactic acid-glycolic acid copolymer, the method comprising:
   mixing a first granular porous substance including the one of poly-D-lactic acid and poly-L-lactic acid with a second granular porous substance including the lactic acid-glycolic acid copolymer to prepare a mixture; and
   pressurizing and heating the mixture in a mold,
   wherein in the heating, the mixture is heated to a temperature greater than or equal to a melting point of the lactic acid-glycolic acid copolymer and less than a melting point of the one of poly-D-lactic acid and poly-L-lactic acid.

* * * * *